United States Patent
Pang et al.

(10) Patent No.: US 10,371,698 B2
(45) Date of Patent: Aug. 6, 2019

(54) SAMPLE TESTING APPARATUS AND METHOD

(71) Applicant: ALERE TOXICOLOGY PLC, Oxfordshire (GB)

(72) Inventors: Alan Pang, Oxfordshire (GB); Gordon Jowett, Oxfordshire (GB); Barry Lillis, Oxfordshire (GB); Jack Fairbank, Oxfordshire (GB)

(73) Assignee: ALERE TOXICOLOGY PLC, Oxfordshire (GB)

( * ) Notice: Subject to any disclaimer, the term of this patent is extended or adjusted under 35 U.S.C. 154(b) by 94 days.

(21) Appl. No.: 15/606,631

(22) Filed: May 26, 2017

(65) Prior Publication Data

US 2018/0017548 A1    Jan. 18, 2018

Related U.S. Application Data

(62) Division of application No. 14/509,192, filed on Oct. 8, 2014, now Pat. No. 9,664,673, which is a division
(Continued)

(30) Foreign Application Priority Data

Aug. 25, 2010  (GB) .................................. 1014167.9

(51) Int. Cl.
  *B01L 3/00*   (2006.01)
  *G01N 33/53*  (2006.01)
  *G01N 33/559* (2006.01)

(52) U.S. Cl.
  CPC .... *G01N 33/5302* (2013.01); *B01L 3/502715* (2013.01); *G01N 33/53* (2013.01);
(Continued)

(58) Field of Classification Search
None
See application file for complete search history.

(56) References Cited

U.S. PATENT DOCUMENTS

2002/0001539 A1   1/2002  Dicesare et al.
2003/0153021 A1   8/2003  Lu et al.
(Continued)

FOREIGN PATENT DOCUMENTS

GB   2339615 A    2/2000
WO   97/34698 A1  9/1997
(Continued)

OTHER PUBLICATIONS

International Search Report, dated Aug. 23, 2011, and Written Opinion, issued in International Application No. PCT/GB2011/050935.
(Continued)

*Primary Examiner* — Rebecca L Martinez
(74) *Attorney, Agent, or Firm* — Casimir Jones S.C.; Thomas Isenbarger

(57) ABSTRACT

Apparatus for performing an assay to detect the presence of an analyte in a test sample. A housing defines a slot for receiving a sample collector, and a capsule contains a buffer liquid, the capsule being sealed by an openable lid, and being connected to the housing such that insertion of a sample collector into the slot causes the lid to open releasing the buffer liquid into the slot. The housing further defines an incubation chamber containing or configured to receive a reagent, and an aperture permitting liquid communication between the slot and the incubation chamber. The apparatus comprises one or more test elements, a substantially liquid tight sealing member separating the incubation chamber and the test element(s), and an activation mechanism operable to open the liquid tight sealing member thereby bringing at
(Continued)

least a portion of the or each test element into liquid communication with the incubation chamber.

10 Claims, 9 Drawing Sheets

Related U.S. Application Data of application No. 13/818,885, filed as application No. PCT/GB2011/050935 on May 16, 2011, now Pat. No. 8,883,489.

(52) U.S. Cl.
CPC .......... *G01N 33/559* (2013.01); *B01L 3/5023* (2013.01); *B01L 2200/04* (2013.01); *B01L 2200/0689* (2013.01); *B01L 2200/16* (2013.01); *B01L 2300/0636* (2013.01); *B01L 2300/0672* (2013.01); *B01L 2300/0681* (2013.01); *B01L 2300/0825* (2013.01); *B01L 2300/1827* (2013.01); *B01L 2400/0677* (2013.01); *B01L 2400/0683* (2013.01)

(56) References Cited

U.S. PATENT DOCUMENTS

| | | |
|---|---|---|
| 2003/0158499 A1 | 8/2003 | Smith et al. |
| 2003/0180815 A1 | 9/2003 | Rawson et al. |
| 2005/0196820 A1* | 9/2005 | Zweig .................. C12Q 1/004 435/14 |
| 2006/0275922 A1 | 12/2006 | Gould et al. |
| 2007/0031283 A1 | 2/2007 | David et al. |
| 2007/0184492 A1 | 8/2007 | Wang et al. |
| 2008/0166820 A1 | 7/2008 | Gould et al. |
| 2008/0199851 A1* | 8/2008 | Egan .................... B01L 3/5023 435/5 |
| 2009/0021728 A1 | 1/2009 | Heinz et al. |
| 2010/0206055 A1 | 8/2010 | Abbott et al. |

FOREIGN PATENT DOCUMENTS

| | | |
|---|---|---|
| WO | 0004381 A1 | 1/2000 |
| WO | 2005/045408 A1 | 5/2005 |
| WO | 2007/098184 A2 | 8/2007 |
| WO | 2008086401 A2 | 8/2007 |
| WO | 2008/055257 A2 | 5/2008 |
| WO | 2009/024773 A1 | 2/2009 |
| WO | 2010/036808 A1 | 4/2010 |

OTHER PUBLICATIONS

International Preliminary Report on Patentability, dated Dec. 6, 2012, issued in International Application No. PCT/GB2011/050935.
GB Search Report, dated Dec. 6, 2010, issued in priority GB Application No. GB1014167.9.
Jehanli, A., Brannan, S., Moore, L., and Spiehler, V., "Blind Trials of an Onsite Saliva Drug Test for Marijuana and Opiates," Journal of Forensic Sciences, vol. 46, No. 5, 2001, pp. 1214-1220.

\* cited by examiner

SAMPLE TESTING APPARATUS AND METHOD

CROSS REFERENCE TO RELATED APPLICATIONS

This application is a division of U.S. application Ser. No. 14/509,192, filed Oct. 8, 2014, which is a division of U.S. application Ser. No. 13/818,885, filed Feb. 25, 2013, which claims the priority of PCT/GB2011/050935, filed on May 16, 2011, which claims priority to Great Britain Application No. 1014167.9, filed Aug. 25, 2010, the entire contents of each of which is hereby incorporated in total by reference.

TECHNICAL FIELD OF THE INVENTION

The present invention relates to a sample testing apparatus and method and in particular, though not necessarily, to an apparatus and method for facilitating specific binding assays to identify, for example, the presence of drugs of abuse in samples. Such testing may employ lateral flow based testing procedures.

BACKGROUND OF THE INVENTION

A specific binding assay is an assay that provides a biochemical test for detecting the presence or concentration of a substance in solutions that frequently contain a complex mixture of substances. An example of a specific binding assay is the immunoassay. Immunoassays rely on the ability of an antibody to bind with high specificity to one or a very limited group of molecules. A molecule that binds to an antibody is called an antigen. Immunoassays can be carried out to detect the presence in a solution of either member of an antigen/antibody pair. For antigen detection (i.e. where the antigen is the analyte), an antibody that specifically binds to that antigen can be prepared for use as an analytical reagent. When the analyte is a specific antibody its cognate antigen can be used as the analytical reagent. In either case the specificity of the assay depends on the degree to which the analytical reagent is able to bind to its specific binding partner to the exclusion of all other substances that might be present in the sample to be analyzed. In addition to the need for specificity, a binding partner must be selected that has a sufficiently high affinity for the analyte to permit an accurate measurement. The affinity requirements depend on the particular assay format that is used.

A competitive binding immunoassay is a particular example of the immunoassay. This may be better understood by considering the specific example of a test for a particular drug molecule, e.g. cocaine. In this case, a sample is obtained from a subject suspected of having taken the drug. This may be a saliva, blood or a urine sample. The sample is then mixed with a solution containing an antibody for that drug. Typically, these antibodies are labelled with some detectable marker, e.g. a gold particle, fluorescent marker, etc. If the drug is present, the labeled antibody molecules are all bound to the drug molecules. The mixture is then exposed to a test element to which drug molecules being tested for are bound. If the drug is present in the sample, then there will be no free labeled antibodies available to bind to the test element. No detectable change will occur. If, on the other hand, no drug is present in the sample, free labeled antibodies will be available and will bind to the test element. A detectable change will occur. The skilled person will appreciate that, rather than binding the drug molecules themselves to the test element, analogues of the drug molecule may be bound, i.e. molecules possessing the relevant binding group or groups.

Competitive binding immunoassays may be performed using a lateral flow device. Such a test methodology is described in GB Patent 2339615 of Cozart Bioscience Limited, corresponding published International Application WO 00/04381, and Journal of Forensic Science 2001, volume 46, pages 1214-1220. A common feature of lateral flow devices for analyte detection is the provision of a test strip or sheet comprising a dry porous material such as nitrocellulose through which a liquid sample can be drawn to reach one or more spatially distinct analyte detection zones. Each such zone presents an immobilised specific binding reagent.

FIG. 1 illustrates schematically a test strip for use in carrying out a lateral flow immunoassay in which reference numeral 1 identifies a porous strip of nitrocellulose sheet laminated onto a backing support, numeral 2 identifies the analyte detection zone presenting immobilised analyte (or an analogue of the analyte), numeral 3 identifies a control zone presenting immobilised antibody to capture labelled antibody, numeral 4 is a label release pad which releases labelled antibody into liquid drawn into this pad from the sample receiving pad, numeral 5, and numeral 6 identifies a wicking pad.

GB2339615 also describes apparatus for reading results of tests carried out using a lateral flow test strip of the type illustrated in FIG. 1. According to the described approach, test strips are integrated into a disposable cartridge, the disposable cartridge holder comprising a swab holder for receiving the end of a swab onto which a test sample (e.g. saliva) has been placed. To perform a test, the swab holder is filled with a buffer solution and the swab inserted. (The swab holder may be pre-filled and the top sealed with a removable foil lid.) The test sample mixes with the buffer solution and is soaked onto and through the test strip. The cartridge is inserted into a reader and, following some incubation period, e.g. 5 minutes, an optical reading performed. Results are displayed on a digital display. Prior art immunoassays of the type described in GB2339615 rely upon a pre-mixing of the test sample with a buffer solution, and a subsequent washing of the solution through the zone containing the labelled antibody and into the test strip.

US patent application publication number US2006/0275922 describes a lateral flow immunoassay test device that facilitates a first pre-mixing of a sample with a buffer, and a second pre-mixing of the mixed sample and buffer with a dry reagent which may be an antigen or a labelled antibody.

An alternative to the competitive binding immunoassay is the so-called sandwich binding immunoassay. In such sandwich assays, binding of the analyte occurs at a minimum of two sites by two antibody moieties. The first moiety is labelled as a reagent whilst the second is immobilised to the test strip. Therefore, the appearance of a visual indication is an indication of a positive test result.

SUMMARY OF THE INVENTION

According to a first aspect of the present invention there is provided apparatus for use in performing an assay to detect the presence of an analyte or analytes in a test sample. The apparatus comprises a housing defining a slot for receiving a sample collector, and an incubation chamber containing or configured to receive a reagent, and an aperture permitting liquid communication between said slot and said incubation chamber. The housing further defines a capsule containing a buffer liquid, the capsule being sealed by an openable lid, and the capsule being connected to the housing in such relation with said slot and said aperture that insertion of the sample collector into the slot causes the lid to open releasing the buffer liquid into the slot under pressure to communicate a portion of the sample to the incubation chamber via the aperture. The apparatus further comprises one or more test elements, a substantially liquid tight sealing member separating said incubation chamber and said test element(s), and an actuation mechanism operable to open said liquid tight sealing member thereby bringing at least a portion of the or each test element into liquid communication with said incubation chamber.

Embodiments of the present invention allow for optimisation of an assay by pre-mixing a sample solution with a reagent, prior to introducing the mixed solution to the test element(s).

The openable lid may be a ruptureable lid.

The capsule may be substantially axially aligned with said slot such that insertion of a sample collector into the slot causes the collector to impact and open said lid.

The slot may have internal dimensions to permit a substantially liquid tight seal to be formed between the housing and an inserted sample collector, thereby retaining the released buffer liquid within the housing. The slot may also have internal dimensions such that insertion of a sample collector into the capsule exerts a force on the buffer liquid causing the liquid to flow at least partially through the collector, and through said aperture into the incubation chamber. This arrangement reduces the number of user steps required to carry out a test.

The liquid tight sealing member may be a ruptureable seal.

The actuation mechanism may comprise a trigger accessible via an opening defined by said housing such that the trigger can be engaged by a firing mechanism external to the housing.

The or each test element may comprise a test strip for performing a lateral flow assay, in which case said actuation mechanism may comprise a plate located above the or each test strip, a pivot rod fixed to the plate, and a pivot support defined by said housing, said trigger being attached to the plate or pivot rod such that a force applied to the trigger causes the plate to rotate, forcing it against the or each test strip and in turn forcing the test strip(s) against said liquid tight sealing member causing the said liquid tight sealing member to open. The housing may define a support platform for partially supporting the or each test strip such that the or each test strip is bent over an edge of the platform upon operation of said activation mechanism.

The actuation mechanism may alternatively be implemented by providing said substantially liquid tight sealing member as a dissolvable member.

The apparatus may comprise a pad within said incubation chamber, said reagent being supported by said pad. The reagent may be located within or adjacent to said aperture.

The housing may further define a window through which at least a portion of the or each said test element is visible from the exterior of the housing.

Said aperture extends substantially parallel to said slot. The apparatus may comprise a filter located within or adjacent to said aperture.

The reagent and the test element(s) may be configured to allow an immunoassay to be performed, and in particular to allow one of a competitive binding or a sandwich binding immunoassay to be performed.

The apparatus may be configured as a cartridge to be received by a reading system for the purpose of reading a test result or results from the apparatus. The cartridge may be disposable.

According to a second aspect of the invention there is provided a reading system adapted for use with an apparatus according to the above first aspect of the invention, the system comprising a housing defining a slot for receiving the apparatus, an actuator for operating the activation mechanism of the apparatus, and a reading mechanism for taking a reading from the or each test element.

Further aspects of the invention are set out in the appended claims.

DETAILED DESCRIPTION OF THE INVENTION

As has been discussed above, prior art approaches to lateral flow immunoassay tests have generally relied upon a pre-mixing of the test sample with a buffer, and a subsequent washing of the buffer through a dry portion of the test strip to which the labelled antibody is bound. Experiments have shown that improved detection sensitivity can be obtained by allowing the buffer/sample solution to pre-mix with the dry, labelled antibody for a period of time, prior to allowing the solution to flow through the test strip. Whilst the approach is described in the following with respect to a competitive binding type assay, it will be appreciated that it is equally applicable to a sandwich binding type assay, as well as to other assay types.

Figure 2:
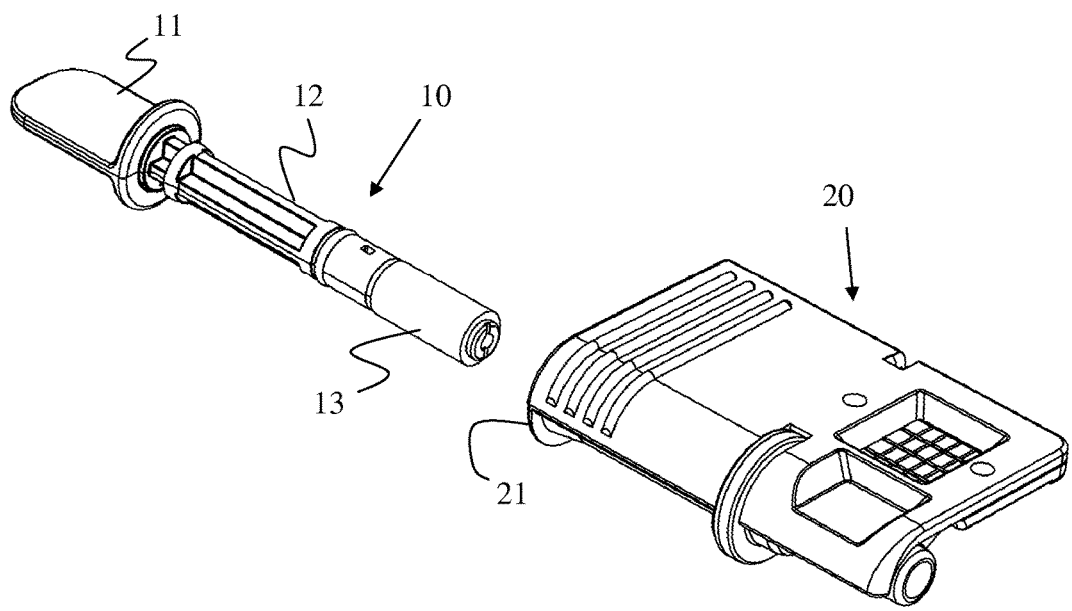
FIG. 2 illustrates a sample collector and a cartridge for receiving the collector.

FIG. 2 illustrates a collector 10 formed substantially of a rigid plastics material. The collector comprises a handle 11 at one end, and a generally cylindrical body 12. At the end remote from the handle, a swab 13, formed of a fibrous and absorbent material such as cotton, polyester or hydrophillic foam, is supported by the body 12. In use, a subject is asked to place the swab in the mouth, thereby causing saliva to be absorbed into the swab. Of course, samples may be obtained by other means, e.g. dipping the swab end of the collector into a urine sample. In order to aid sample collection, the outer surface of the swab may be formed with corrugations, for example in the form of a multiplicity of ribs extending axially along the swab 13. Such an arrangement may overcome issues with thick, high mucus salivas, by increasing the surface area of the swab as much as possible and thereby slowing the tendency for the surface of the swab to block up with mucus and thereby increase the uptake. The swab 13 may also be made from a dual density material. The inside layer is of relatively high density to give good mechanical attachment to the collector handle, whilst the outer layer is of relatively low density (preferably of the lowest density possible) to give rapid collection and minimise drug retention.

The collector 10 may be a collector as marketed by Concateno (Abingdon, UK) under the CERTUS brand name.

Figure 3:
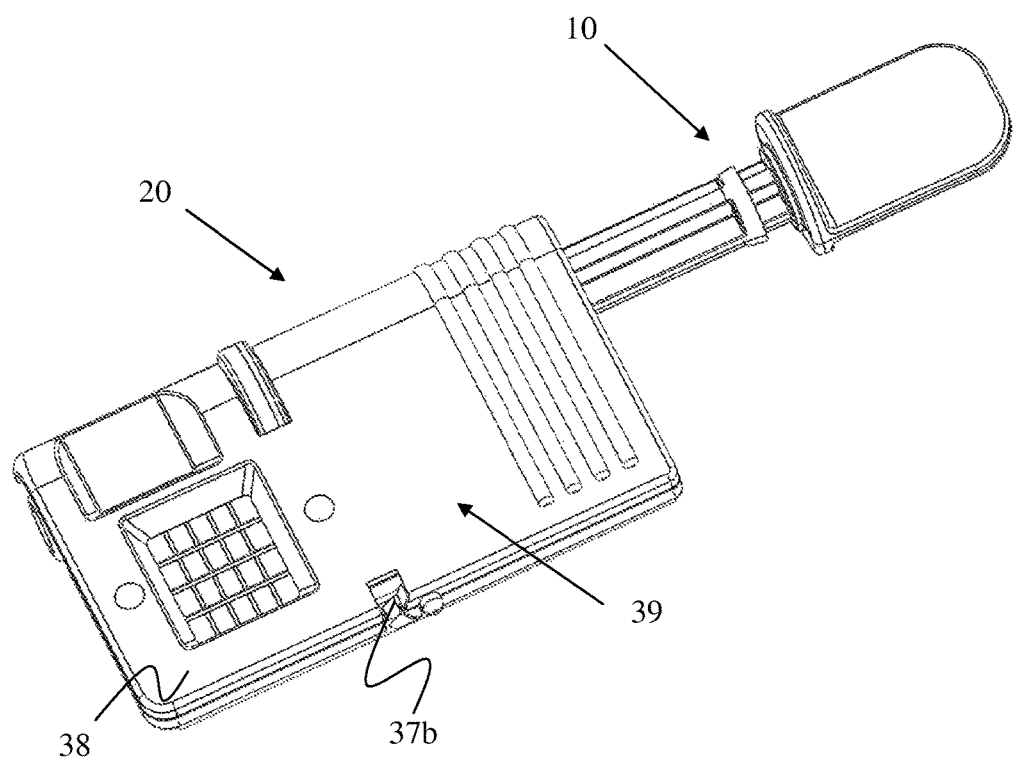
FIG. 3 illustrates the sample collector of FIG. 2 fully inserted into the cartridge.
Figure 4:
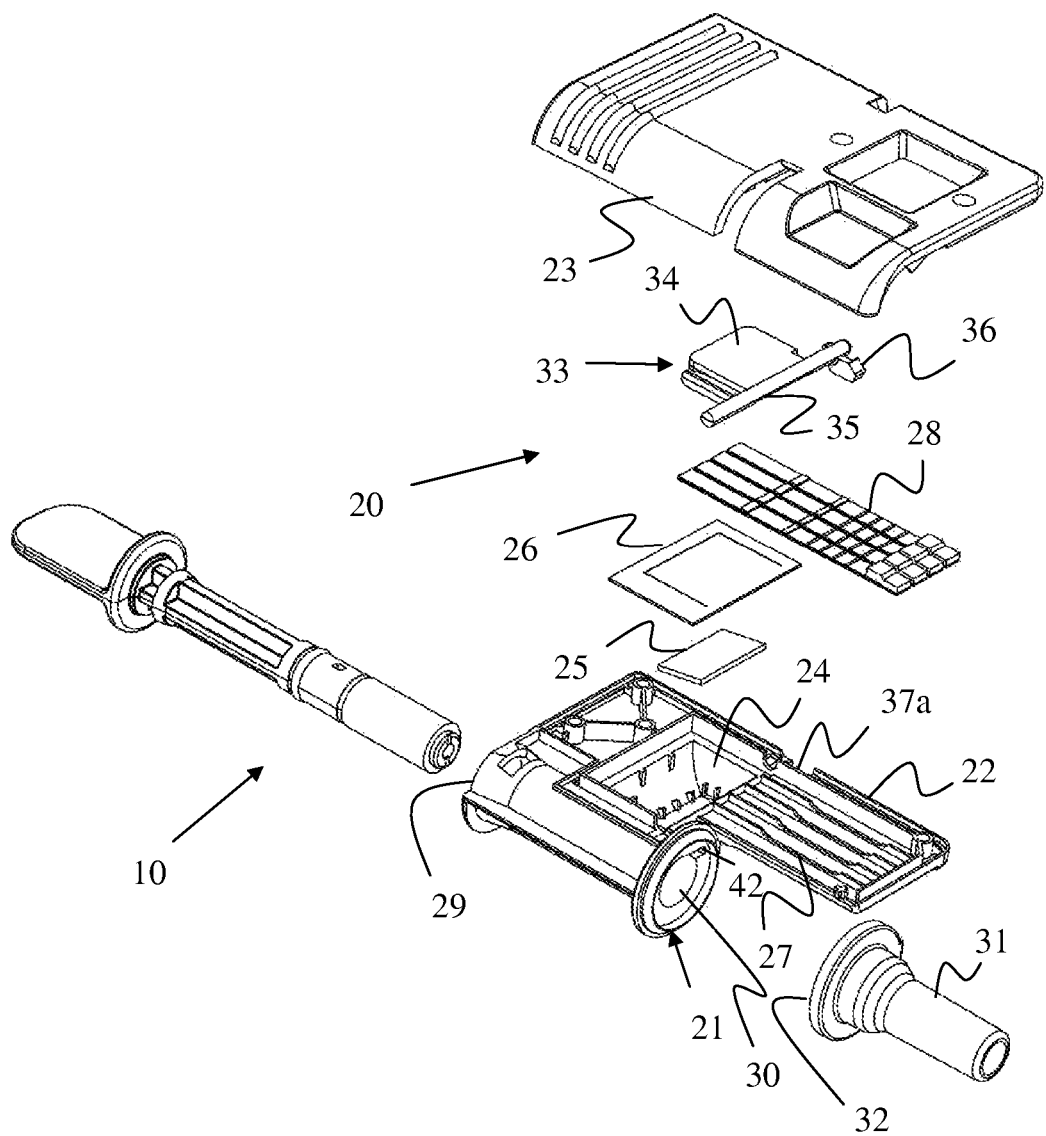
FIG. 4 is an exploded view of the cartridge of FIG. 2, also showing the sample collector.

FIG. 2 further illustrates a disposable cartridge 20 having an opening and slot 21 for receiving the collector 10. FIG. 3 illustrates the collector 10 fully inserted into the cartridge. The cartridge is further illustrated in the exploded view of FIG. 4. In particular, the cartridge comprises a main cartridge housing 22 and a cartridge cover 23, both formed of a rigid plastics material. The housing and cover are configured so as to be snap-fitted together during assembly. The housing 22 is moulded to provide an incubation well 24, into which is placed a reagent pad 25. The pad 25 is impregnated a reagent, e.g. gold labelled antibodies or other labelled antibodies. As an alternative to including the reagent into the well 24 by fixing it to a pad 25, the reagent may merely be deposited onto a surface of the well, or dropped into the well as a pellet.

The well containing the pad 25 is sealed with a hydrophobic separation layer 26 which sits above the pad 25. The separation layer may, for example, be provided by a sheet of flexible plastic, metal foil, or the like. A particularly advantageous structure for the separation layer comprises a lower foil layer in combination with an upper, thin layer of plastic. A rectangular frame of absorbent material is provided on top of the plastic layer. The plastic layer is removed within the rectangular window. The provision of the plastic layer facilitates thermal welding of the layer 26 to the cartridge.

Figure 1:
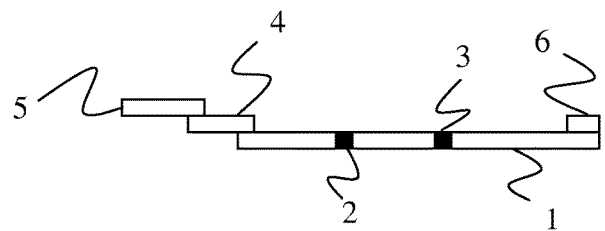
FIG. 1 illustrates a lateral flow test strip suitable for performing an immunoassay.

The cartridge housing 22 is also moulded to provide tracks 27 for receiving and supporting a plurality (in this case four) of lateral flow test strips 28. During assembly, a test strip 28 is placed into a corresponding one of the tracks 27 such that one end of the strip is overlaid onto the top surface of the separation layer 26. Each strip may be configured to test for a different analyte. The strips are similar in structure to that illustrated in FIG. 1, except that they do not comprise the label (reagent) release pad (reference numeral 4 of FIG. 1). This is not required as the labelled reagent is impregnated into the pad 25. It is advantageous to overcoat the upper surface of the test strip with thin layer of transparent plastic. This provides added strength to the strip, helping to prevent the separation of the various layers of the strip, particularly when the strip is bent (as will be described further below). Also provided at one side of the cartridge housing is a trigger access opening 37a. It is of course possible that one or more of the strips may still include a labelled reagent (FIG. 1), e.g. where pre-incubation in the well 24 is not required. For these strips, some other reagent that is required or advantageous, may still be attached to the pad 25 or otherwise introduced to the well during testing.

Considering further the collector receiving slot 21, this has a generally cylindrical shape. The slot 21 has circular openings at both ends 29,30, as well as an opening 42 into the incubation well 24. The opening 42 is provided as a secondary slot or "lumen" running parallel to the main slot 21. The opening 42 runs from the end surface of the slot 21 into the incubation well 24. The size of the secondary slot is designed to minimise "dead" volume but also deliver the material into the incubation well under the required pressure to actively start re-hydration of the reagent. The entrance to this secondary slot 42 may also feature an additional 'flat' filter, designed as a means to filter out debris. The secondary slot 42 may alternatively be filled with a slug/cylinder of porous material to achieve a similar function but could also be used as an additional reagent position or for additional sample 'cleaning' components.

The cartridge further comprises a buffer capsule 31 formed of a rigid plastics material. An open end of the capsule is sealed with a thin foil seal 32. The capsule 31 is sonic welded or otherwise fixed to the end 30 of the collector receiving slot 21.

The cartridge 20 further comprises an actuation paddle 33 that is formed as a discrete component. The actuation paddle 33 comprises a substantially rectangular plate 34 integrally formed with a pivot rod 35. The pivot rod is supported at both ends within the cartridge cover 23. The plate 34 sits directly above and in contact with the ends of the test strips 28. A trigger 36, formed integrally with the pivot rod 35, projects from one end of the pivot rod. As is shown in FIG. 3, a trigger receptor 37b is formed in the cartridge cover 23 such that the trigger 36 is able to move into the receptor as it is pushed from below. The trigger may comprise some form of anti-tamper mechanism, for example to prevent accidental activation prior to insertion of the cartridge into a reading system (see below). This may require for example that the trigger be moved in two substantially orthogonal directions to achieve activation. Also shown in FIG. 3 is a reading window 38 formed in the casing cover, and which gives visual access to the test strips and in particular to the respective analyte detection and control zones.

An optional barcode 39 is printed or otherwise provided on an upper surface of the cartridge cover 23. This barcode can be read by an optical reading system (described below) and provides information such as the type of lateral flow test being conducted, "use by date" information, calibration data, etc.

Figure 5:
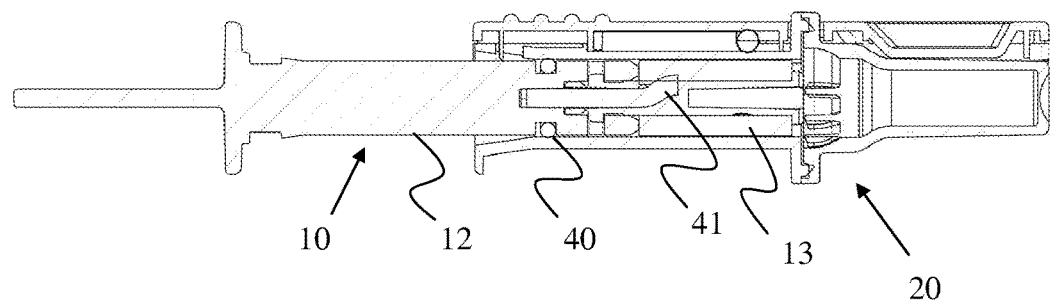
FIG. 5 is a cross-sectional view of the cartridge of FIG. 2 with the sample collector fully inserted.

Referring now to the cross-sectional view of FIG. 5, this shows the collector 10 fully inserted into the cartridge 20. This view shows an 'O' ring 40 that fits within a recess extending circumferentially around the body 12 of the collector 10. This provides a substantially liquid tight seal between the collector and the inner wall of the receiving slot 21 when the handle is fully inserted. FIG. 5 also shows an indicator rod 41 which extends axially along the inside of the collector body 12, and which is in fluid communication with an inner surface of the swab 13. As is known in the art, the indicator rod is able to provide a visual indication when sufficient sample has been absorbed by the swab. The indicator rod 41 does not play any further part in the lateral flow test. The indicator rod 41 may be chosen for its wicking rate as this will influence the speed at which the visual indication appears, allowing more sample to be collected.

It will also be clear from FIG. 5 that full insertion of the collector 10 into the receiving slot 21 within the cartridge will cause the foil seal 32 to be ruptured. Although this may be facilitated by appropriately shaping the end of the handle body that projects beyond the swab, it is desirable to avoid forming any sharpened elements on the end of the collector (and which could result in injury to a user or donor). An alternative design may be to provide a set of radially projecting teeth around a portion of the opening into the buffer capsule that is covered by the foil seal. The teeth extend around approximately 180 degrees of the opening, and project radially inwardly to an extent such that, when the swab end of the collector is pushed against the foil seal, the seal breaks along the portion where the teeth are present, forming a flap which is pushed into the capsule. The swab may be compressed slightly by the teeth, allowing the swab to be pushed further into the capsule. The capsule may narrow along its length to facilitate further squeezing of the swab 13.

The rupture of the foil seal 32 by the collector, and the subsequent movement of the swab into the buffer capsule 31, causes buffer solution to be forced into and through the swab material, mixing with sample fluid as it travels. The pressure further causes the mixed fluid to be driven into the incubation well 24 through the opening 42. As the well 24 is filled, the reagent pad 25 is hydrated, releasing the attached labelled antibodies. It will be appreciated that the sealing facilitated by the O-ring 40 and the inner surface of the slot 21 is formed prior to rupture of the seal 32 in order to prevent buffer solution escaping through the slot opening 29. The actual position at which the seal is formed within the slot may be adjusted in order to tune the volume of fluid delivered into the incubation well 24 from the buffer capsule.

Figure 6:
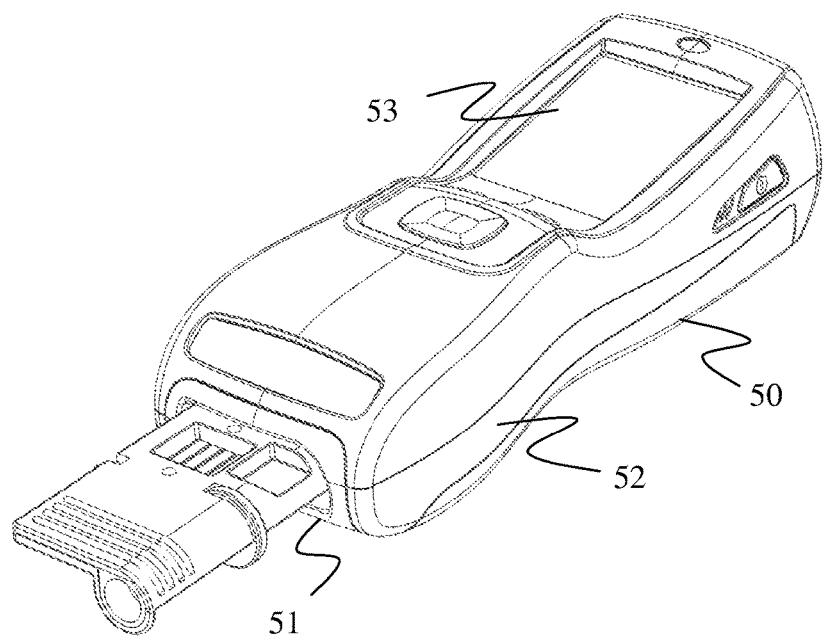
FIG. 6 illustrates schematically an optical reading system which the cartridge of FIG. 2 partially inserted into the system.

FIG. 6 illustrates schematically an optical reading system 50. This system has a cartridge receiving slot 51 appropriately shaped to receive the cartridge 20. The system has an (internal) optical reading mechanism 52 comprising light emitters and detectors and appropriate electrical and electronic components. These will not be described in any further detail as their construction will be readily apparent to the skilled person. Suffice to say that the mechanism 52 is able to detect optical changes occurring in the test strips 28, and in particular to detect changes in the analyte detection and control zones. A display 53 is provided for presenting the results of a test to a user. The reading system may further comprise a mechanism for detecting an angle at which the system is held. This may be in the form of an accelerometer. The display 53 may be used to notify the user when the system is not being held at the correct angle.

Figure 8A:
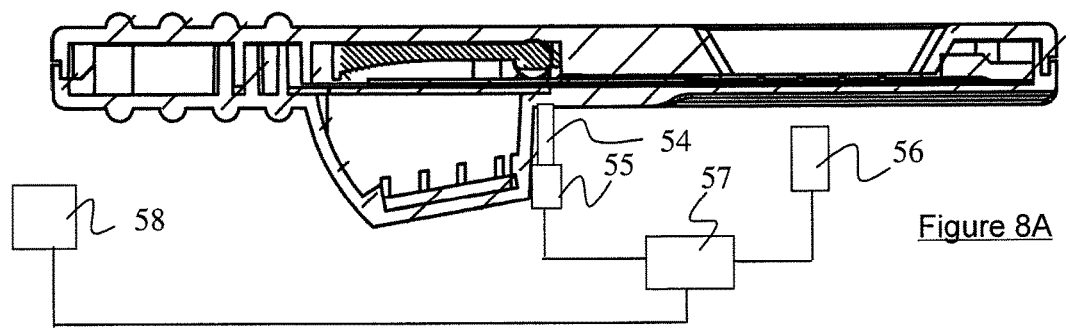
FIG. 8A is a cross-sectional view of the cartridge of FIG. 2 with the sample collector fully inserted, according to a first operational configuration.
Figure 8B:
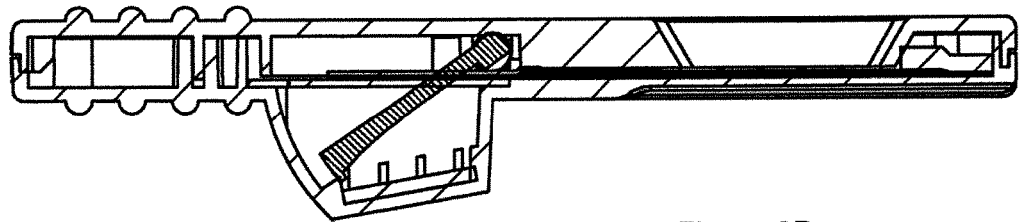
FIG. 8B is a cross-sectional view of the cartridge of FIG. 2 with the sample collector fully inserted, according to a second operational configuration.

The optical reader further comprises a trigger actuation rod 54 that is moved up and down by a solenoid actuator 55 or the like (see FIGS. 8A and 8B discussed below). When a cartridge is fully inserted into the cartridge receiving slot 51, the rod 54 is located directly beneath the trigger access opening 37a formed in the cartridge housing 22. The optical reading system further comprises a cartridge insertion detector 56 which is configured to detect full insertion of a cartridge into the reading system. The detector 56 is coupled to a computer 57, which in turn controls the solenoid actuator 55 and the optical reading mechanism 52. The detector 56 may make use of a mechanical switch, or an optical detector. A further optical detector 58 is also coupled to the computer 57 and is configured to detect insertion of the collector into the capsule 31.

Figure 7:
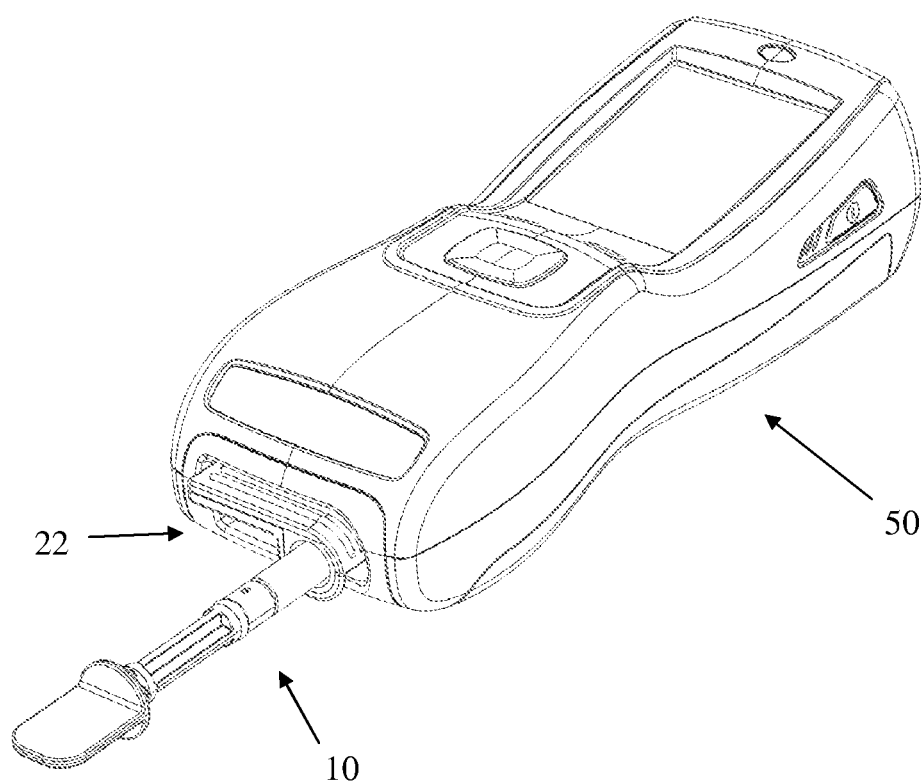
FIG. 7 illustrates the cartridge reading system with the cartridge of FIG. 2 fully inserted into the system and with the collector of FIG. 2 partially inserted into the cartridge.

Considering further the operation of the test procedure, the user inserts the cartridge into the cartridge receiving slot 51 in the optical reading system 50. FIG. 7 illustrates the cartridge fully inserted into the optical reading system. The user then collects a sample from a subject and inserts the collector 10 into the cartridge 20, causing release of the buffer fluid into the incubation well 24 and hydration of the bound labelled antibody. It is noted here that separation layer 26 may be formed such that, whilst preventing the flow of liquid from the incubation well 24 into the area containing the test strips, it does allow venting of air from the well to that area. This may be useful in preventing pressurisation of the well 24 during insertion of the collector into the cartridge.

Insertion of the cartridge is detected by the detector 56, and this status change is relayed to the computer 57. The computer initiates a first timer. The timer delay is set to an appropriate period, e.g. 1 minute. This period may be used to pre-heat the test strips 28 (see below). When the timer expires, a message is displayed requesting that the user insert a collector 10 which has been used to collect a sample. The detector 58 is used to detect rupture of the foil seal 32 and hence full insertion of the collector. The detector 58 sends an appropriate signal to the computer 57. The computer 57 reacts by commencing a second timer, set to a period sufficient to allow full rehydration of the reagent in the incubation well. When this timer expires, the computer sends a signal to the solenoid actuator 55, causing the trigger actuation rod 54 to be pushed up through the trigger access opening 37a formed in the cartridge housing 23 and into contact with the trigger 36. Further force applied to the trigger actuation rod 54 pushes the trigger 36 up, where it is accommodated within the trigger receptor 37b. Of course, this movement of the trigger 36 causes the attached rod 35 and plate 34 to rotate about the rod axis, forcing the plate 34 against the ends of the test strips 28. FIGS. 8A and 8B illustrate the cartridge (upper view) with the plate in the initial position prior to actuation, and (lower view)with the plate in the fully rotate position (NB. FIG. 8A illustrates various internal components of the optical reading system as described above, although these are omitted from the lower view). It will be appreciated of course that the cartridge may be designed such that the plate 34 is pushed linearly by the actuator 55, rather than rotationally.

As the plate 34 is pressed against the test strips 28, the strips exert a corresponding force against the separation layer 26. This force causes the separation layer to rupture. [The absence of a plastic coating layer in the centre of the separation layer reduces the strength of the separation layer in the area where the pressure is applied. Rupture of the separation layer 26 may be further facilitated by providing scores or perforations across the separation layer to weaken the layer along these scores.] When rupture occurs, the ends of the test strips 28 are bent and pushed down into the incubation well 24 and into contact with the fluid therein. Fluid is absorbed into the test strips, and flows along the strips past the analyte detection and control zones. A latching mechanism may be employed to lock the plate 34 in the actuated position, such that the solenoid can be deactivated without resulting in removal of the test strips from the incubation well. The provision of a frame of absorbent material around the periphery of the separation layer as described above may help to prevent leakage of fluid from the incubation well 24 which might otherwise come into contact with and damage the optical reading system 50.

Upon actuation of the solenoid mechanism 55, the computer 57 starts a third timer. The duration of the third timer is such as to allow sufficient time for the lateral flow test to complete. Upon expiry of the third timer, the optical reading mechanism 52 performs a measurement on the relevant parts of the strips. Following processing of the results by the computer 57, a result is displayed on the display 53. The user may then remove and dispose of the used cartridge and holder, and commence a further test if desired. It may also be possible for the reading system to monitor the progress of the test as it progresses. This may allow earlier provision of a negative test result.

Although the apparatus and method discussed above have been concerned with a saliva sample, it will be appreciated that they may be used to perform tests on other sample types. For example, they may be used to analyse blood samples or saliva swabs. In the former case, a finger prick is performed, and blood collected using the swab on the collector. Incubation is performed over a longer timescale, e.g. 20 minutes, in order to ensure sufficient time for the buffer to mix with the blood and with the labelled antibodies.

Considering further the geometry of the incubation well 24, this is designed to allow for sample to be held and for the strip ends to remain immersed if the cartridge is tilted. The geometry to hold the pad 25 may comprise a series of ribs which, by minimising the amount of compression of the pad and by holding the pad off the flat 'floor' of the well 24, maximise re-hydration of the reagent and minimise any 'pockets' of un-rehydrated material caused by pinching of the pad material.

In order to improve the efficiency of the mixing of the buffer (containing test sample) and the labelled antibody within the incubation well, the cartridge may be vibrated by an appropriate mechanism within the optical reading system. Alternatively or in addition, the cartridge may be gently heated to ensure an optimum incubation temperature.

Figure 9:
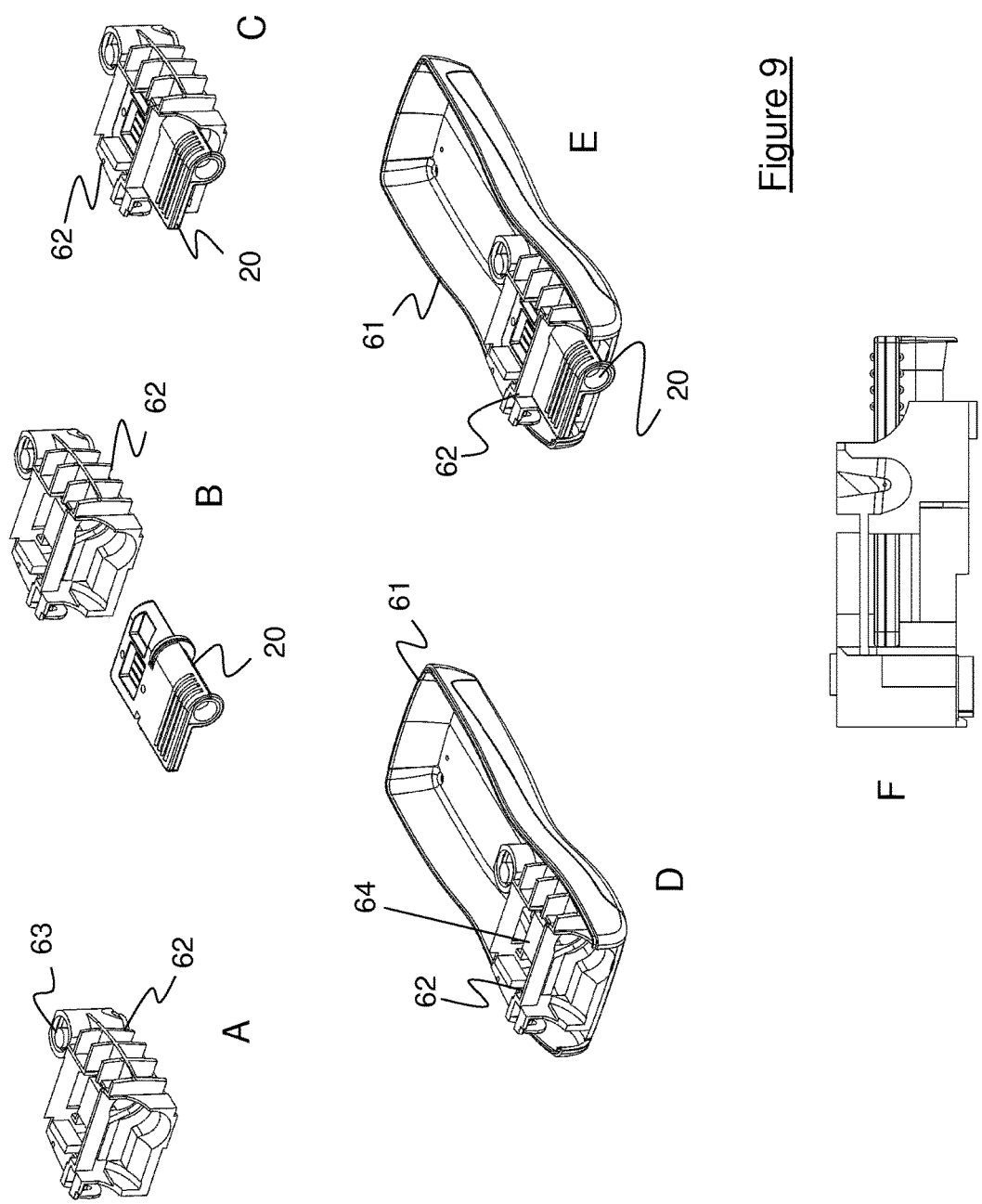
FIG. 9 illustrates various perspective and cross-sectional views of an optical reading system.

FIG. 9 illustrates a particular design of an optical reading system suitable for reading data from a disposable cartridge 20 of the type described above (FIG. 9 omits certain components including the optical and electrical components of the system). The system comprises a lower casing 61 and an upper casing (not shown) which is attached to the lower casing to provide a substantially closed system housing. Located within the lower casing 61 is a cartridge holder 62. The holder 62 is configured such that it is moveable within the casing 61 in the horizontal plane to a small extent. The holder may also be moveable in the vertical plane. Movement is facilitated by a small vibration inducing "motor" 63, fixed within the casing 61 and coupled to the holder 62. The holder 62 also comprises a heating element 64 configured such that, upon insertion of a disposable cartridge 20, the heating element lies beneath the test strips. Both the heating element and the vibration inducing motor are controlled by the computer 57 described above.

The computer 57 may be configured to control the heating element and the vibration inducing motor in order to optimise the lateral flow test. For example, these components may be controlled to achieve pre-heating of the test strip and or reagent prior to insertion of the sample collector, heating of the incubation well following insertion of the collector, and vibration of the incubation well following insertion of the collector. The times and durations for which these steps are performed are determined, for example, based upon empirical observations.

Figure 10:
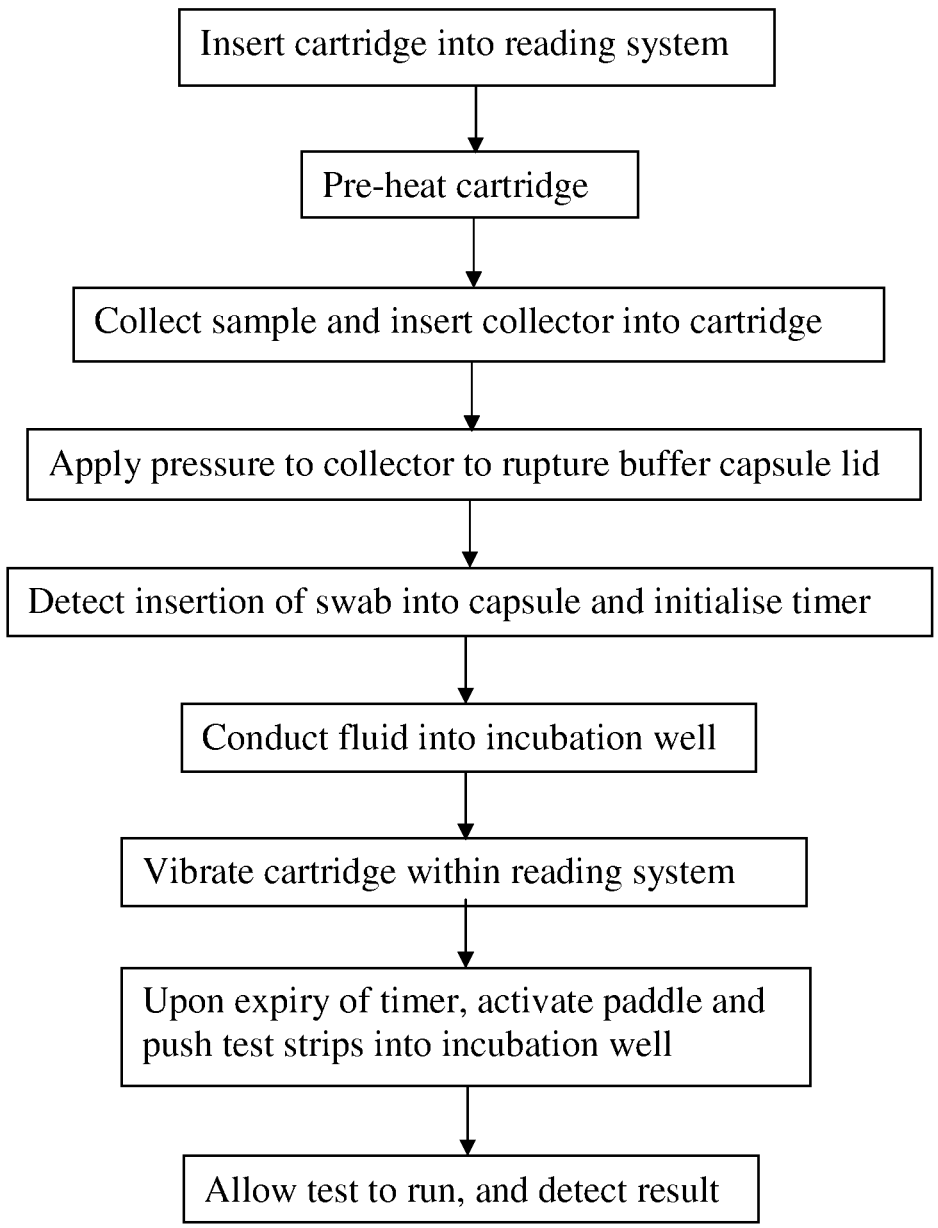
FIG. 10 is a flow diagram illustrating a method of performing a lateral flow immunoassay.

FIG. 10 is a flow diagram further illustrating the method described above.

It will be appreciated by the person of skill in the art that various modifications may be made to the above described embodiments without departing from the scope of the present invention. For example, the buffer capsule 32 may be provided with a weakened area into which an end of a syringe may be pushed (i.e. without requiring attachment of a needle to the syringe). Following completion of a test using the optical reading system described, the cartridge and collector may be removed from the system and sent to a laboratory for further testing. Sample remaining in the cartridge may be extracted by inserting a syringe end through the weakened portion of the capsule.

The cartridge described above may be further modified in order to include a third, parallel slot or lumen in order to conduct sample fluid to a second incubation well, such that the cartridge facilitates the performing of two different testing regimes (distinct wells could be provided on either side of the primary slot 21, or a single well could be split into separate sub-wells by a divider). This allows for different reagents to be used for different sets of multiplex assays and solves potential compatibility issues with reagents that need to co-exist in a multi panel test of the pre-incubation format. The cartridge may also be modified such that the separation layer 26 is provided as a dissolvable membrane. Upon injection of fluid into the incubation well 24, the reagent is rehydrated and, over some defined period, the separation layer dissolved. Upon dissolution of the separation layer, the ends of the tests strips are brought into contact with the fluid without the need for the activation paddle 33.

According to a further modification to the above described design, rather than placing the reagent directly into the incubation well 24, this may be located at some point "upstream" of the well. For example, dried reagent may be placed within the opening 42 connecting the slot 21 with the incubation well 24, or may be attached to the outer surface of the foil seal 32 closing the end of the buffer capsule 31. In such embodiments, the released buffer fluid washes the dried reagent and analyte into the incubation well.

According to a still further modification of the above described design, rather than causing the ends of the test strips 28 to bend into the incubation well 24, the activation of the trigger 36 may result in a linear movement of the test strips so that they project into the well. This may be achieved by mounting the test strips onto an appropriately configured shuttle within the cartridge 20.

According to a still further modification of the above described design, the system may be configured to rely upon something other than an optical detection mechanism. For example, magnetic field detection, electrochemical detection and other detection approaches may be used.

Figure 11:
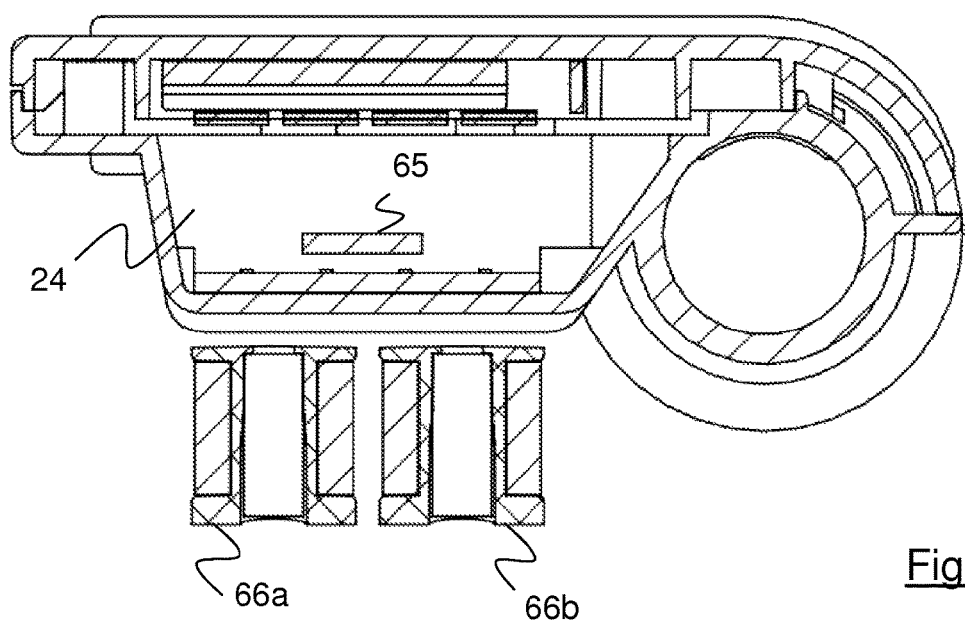
FIG. 11 illustrates schematically a further embodiment of a cartridge for receiving a collector.

According to a still further modification of the above described design, in order to aid mixing of the fluid and reagent within the incubation well 24, a "flea" comprised of a magnetic material may be located within the incubation well 24. The optical reading system is configured to generate a varying magnetic field within the well 24 such that the flea is caused to move about within the well. A cartridge incorporating this design feature is illustrated in cross-section in FIG. 11, where the magnetic flea is identified by reference numeral 65. Also illustrated in FIG. 11 is a pair of cylindrical phase-locked coils 66a, 66b. The coil windings are formed onto custom bobbins with space provided for a field-amplifying metallic core. Such a core may also allow the flea to be held in a known position whilst the coils are inactive, preventing the flea from obstructing other components such as the plate 34 and the test strips 28. The coils 66a, 66b are provided within the optical reading system such that, upon insertion of the cartridge into the system, the coils are located directly beneath the incubation well 24. Other possible sources of a varying magnetic field are a single coil with oscillating supply voltage and moving, permanent magnet.

Whilst the invention has been described above in the context of a lateral flow immunoassay, it will be appreciated that it is also applicable to other forms of assay including DNA assays, and assays that rely upon, for example, microfluidics.

The invention claimed is:

1. A method of performing an assay to detect the presence of an analyte or analytes in a test sample, the method comprising:
   1) inserting a sample collector comprising a swab with a sample into a receiving slot of a cartridge, the cartridge containing one or more test elements, such that insertion of the collector opens a lid of a capsule containing buffer liquid and causes said liquid to be expelled from the capsule under pressure to communicate the buffer liquid and at least a portion of the sample via the slot into an incubation chamber of the cartridge;
   2) mixing the buffer liquid and sample portion with a reagent contained within or introduced into the chamber; and
   3) causing at least a part of each test element to come into contact with the fluid in the chamber, resulting in the lateral flow immunoassay being initiated.

2. A method according to claim 1 and comprising, prior to step 3), inserting the cartridge into a reading system, the system operating to initiate step 3).

3. A method according to claim 2, wherein said cartridge is inserted into the reading system prior to step 1), the method further comprising detecting operation of step 1) and as a result initiating a timer and upon expiry of that timer initiating step 3).

4. A method according to claim 2 and comprising one or both of vibrating and heating the cartridge or a part of the cartridge within the reading system.

5. A method according to claim 4, wherein said cartridge is inserted into the reading system prior to step 1), the method further comprising detecting operation of step 1) and as a result initiating a timer and upon expiry of that timer initiating step 3) and comprising controlling the initiation and duration of one or both of the vibration and heating of the cartridge in dependence upon the timer value.

6. A method according to claim 2 and comprising a step of preheating the cartridge within the reading system prior to step 1).

7. A method according to claim 6 and comprising directing said pre-heating at the test element within said cartridge, and maintaining the test element temperature substantially at a predefined temperature for the duration of the test.

8. A method according to claim 1, wherein said assay is an immunoassay.

9. A method according to claim 8, wherein each test element is a test strip.

10. A method according to claim 1, wherein the step of mixing the reagent with the buffer liquid and sample portion or analyte further comprises applying a varying magnetic field to a magnetic flea located within the incubation chamber.

* * * * *